(12) United States Patent
Nesper et al.

(10) Patent No.: US 7,160,310 B2
(45) Date of Patent: Jan. 9, 2007

(54) SURGICAL DEVICE FOR PUSHING TOGETHER A THREAD LOOP

(75) Inventors: Markus Nesper, Tuttlingen (DE); Klaus-Dieter Steinhilper, Tuttlingen (DE); Dieter Weisshaupt, Immendingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 10/862,788

(22) Filed: Jun. 7, 2004

(65) Prior Publication Data

US 2004/0267287 A1 Dec. 30, 2004

Related U.S. Application Data

(63) Continuation of application No. PCT/EP02/12537, filed on Nov. 9, 2002.

(30) Foreign Application Priority Data

Dec. 15, 2001 (DE) ................................ 101 61 724

(51) Int. Cl.
*A61B 17/03* (2006.01)
*A61B 17/56* (2006.01)
(52) U.S. Cl. ..................... 606/148; 606/72; 606/103
(58) Field of Classification Search ................ 606/110, 606/113, 114, 127, 138–150, 222–233
See application file for complete search history.

(56) References Cited

U.S. PATENT DOCUMENTS

| 2,856,933 | A | | 10/1958 | Hildebrand et al. | |
|---|---|---|---|---|---|
| 4,177,813 | A | | 12/1979 | Miller et al. | |
| 4,765,329 | A | | 8/1988 | Cumming et al. | |
| 4,966,600 | A | | 10/1990 | Songer et al. | |
| 5,021,059 | A | | 6/1991 | Kensey et al. | |
| 5,211,650 | A | * | 5/1993 | Noda | 606/139 |
| 5,242,459 | A | * | 9/1993 | Buelna | 606/148 |
| 5,284,485 | A | * | 2/1994 | Kammerer et al. | 606/148 |
| 5,320,629 | A | * | 6/1994 | Noda et al. | 606/139 |
| 5,433,727 | A | | 7/1995 | Sideris | |
| 5,454,821 | A | | 10/1995 | Harm et al. | |
| 5,466,241 | A | | 11/1995 | Leroy et al. | |
| 5,489,288 | A | * | 2/1996 | Buelna | 606/144 |
| 5,562,684 | A | * | 10/1996 | Kammerer | 606/139 |
| 5,571,120 | A | * | 11/1996 | Yoon | 606/148 |
| 5,919,205 | A | | 7/1999 | Heimberger et al. | |
| 6,096,058 | A | | 8/2000 | Boche | |
| 6,306,159 | B1 | * | 10/2001 | Schwartz et al. | 606/232 |
| 6,319,271 | B1 | * | 11/2001 | Schwartz et al. | 606/232 |
| 2002/0156475 | A1 | | 10/2002 | Lerch et al. | |

(Continued)

FOREIGN PATENT DOCUMENTS

DE           912 619          5/1954

(Continued)

*Primary Examiner*—Glenn K. Dawson
(74) *Attorney, Agent, or Firm*—Lipsitz & McAllister, LLC

(57) ABSTRACT

To avoid a maximum displacing force being exceeded in the case of a device for pushing together a thread loop which is formed by a slip knot at the distal free end of the thread which can be displaced along the thread, with a displacing element which can be displaced on the thread in the direction of the loop, it is proposed that the displacing element or the proximal portion of the thread disposed at the end of the displacing element remote from the loop has connected to it a gripping element which releases the connection between itself and the displacing element or the proximal portion of the thread when a specific holding force is exceeded.

20 Claims, 2 Drawing Sheets

U.S. PATENT DOCUMENTS

2003/0208210 A1* 11/2003 Dreyfuss et al. ............ 606/144
2005/0049599 A1*  3/2005 Nesper et al. ................ 606/72
2006/0135996 A1*  6/2006 Schwartz et al. ........... 606/232

FOREIGN PATENT DOCUMENTS

| DE | 78 02 791 | 5/1978 |
|----|-----------|--------|
| DE | 28 04 070 | 8/1979 |
| DE | 37 09 067 | 9/1988 |
| DE | 89 10 462 | 2/1990 |
| DE | 42 43 427 | 3/1994 |
| DE | 691 08 236 | 8/1995 |
| DE | 694 06 972 | 7/1998 |
| DE | 299 19 090 | 2/2000 |
| EP | 0 602 757 | 6/1994 |
| EP | 0 628 286 | 12/1994 |

* cited by examiner

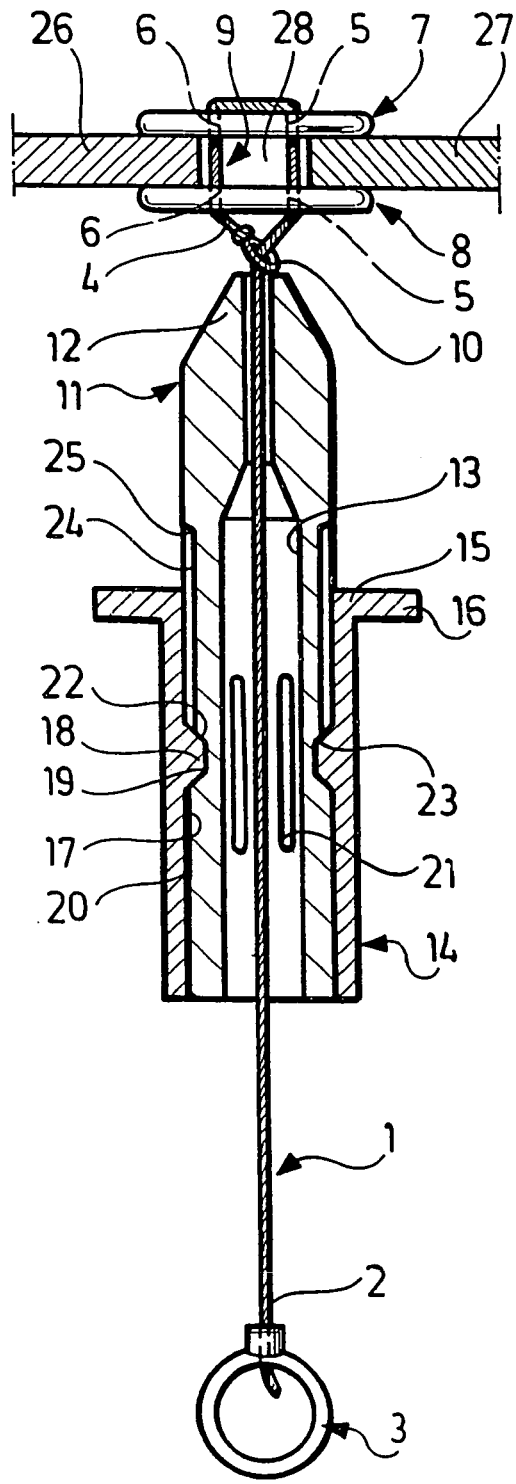
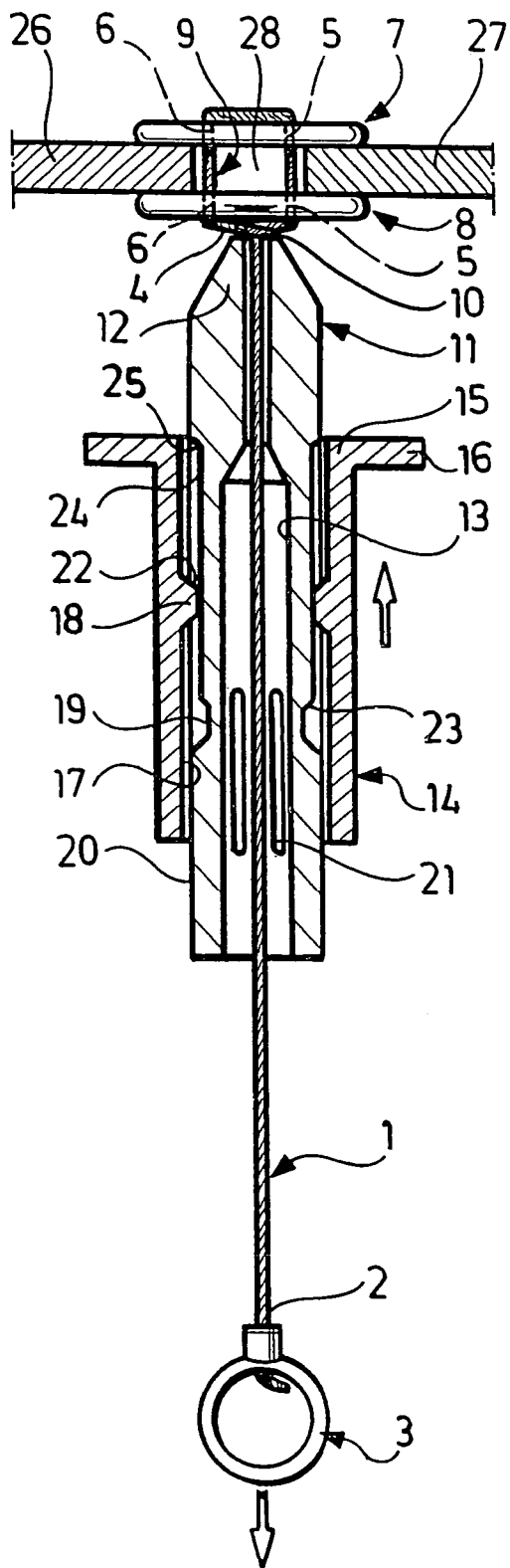

FIG.3
FIG.4
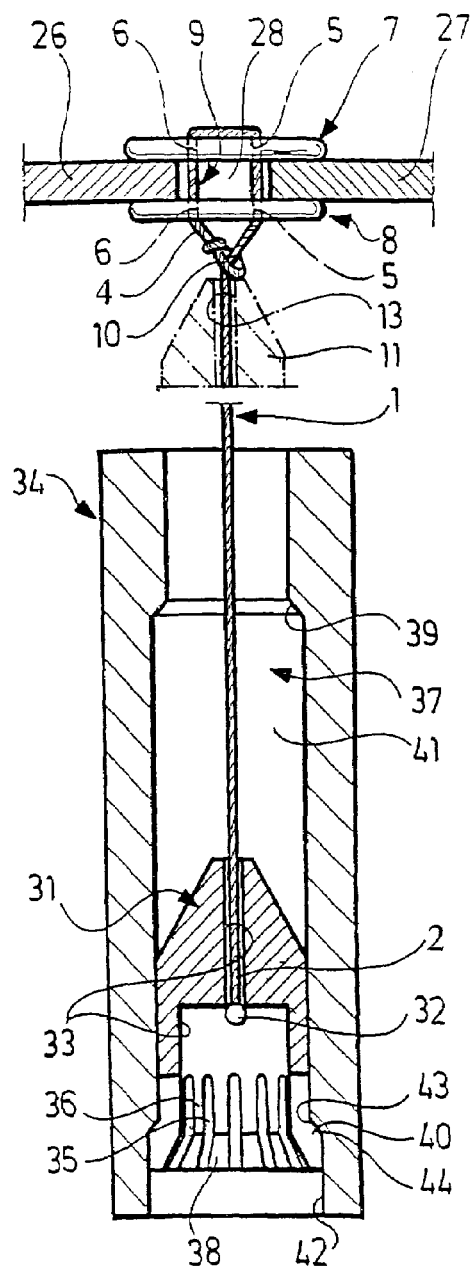
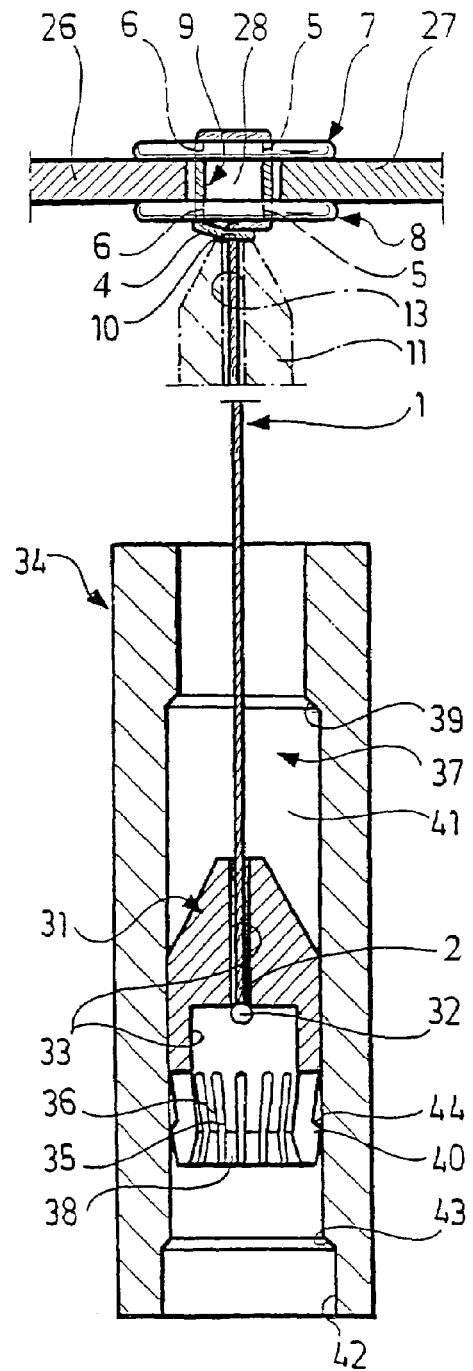

SURGICAL DEVICE FOR PUSHING TOGETHER A THREAD LOOP

This application is a continuation of international application number PCT/EP02/12537 filed on Nov. 9, 2002.

The present disclosure relates to the subject matter disclosed in international application PCT/EP 02/12537 of Nov. 9, 2002, which is incorporated herein by reference in its entirety and for all purposes.

BACKGROUND OF THE INVENTION

The invention relates to a surgical device for pushing together a thread loop which is formed by a slip knot at the distal free end of the thread which can be displaced along the thread, with a displacing element which can be displaced on the thread in the direction of the loop.

Threads are extensively used in the surgical sector to join body parts to one another, to apply ligatures or to connect implant parts to one another or to the body of a patient. When doing so, it is customary to form the thread into a loop at its distal, free end and to connect the free end to the adjoining portion of thread by means of a slip knot, i.e. by means of a knot which can be displaced along the thread by constricting the loop, and which then remains in this position and cannot be pushed back. Such knots are known for example as "Roeder knots".

For displacing the slip knot and for constricting the loop, it is known to dispose a displacing element on the thread, so that the surgeon can draw the loop together simply by securely holding the thread at its proximal end, remote from the loop, and displacing the displacing element on the thread in the direction of the loop, whereby the slip knot is displaced in the direction of the loop, and this leads to a drawing together of the loop.

In certain applications, the drawing together of the loop may cause damage if the loop is tightened too securely. In the case of conventional devices of this type, it was left to the skill of the operator to ensure that the loop was only ever tightened to an extent avoiding such damage, but this entails certain uncertainties.

It is an object of the invention to form a device of the generic type in such a way that excessive tightening of the loop is avoided with certainty.

SUMMARY OF THE INVENTION

This object is achieved according to the invention in the case of a device of the type described at the beginning in that the displacing element or the proximal portion of the thread disposed at the end of the displacing element remote from the loop has connected to it a gripping element which releases the connection between itself and the displacing element or the proximal portion of the thread when a specific displacing force is exceeded.

When the surgeon displaces the displacing element in the direction of the loop to tighten the loop, this takes place in the case of a first variant of the invention by means of a gripping element which is in connection with the displacing element, this connection being released as soon as a specific displacing force is exceeded. This avoids the loop being excessively tightened; the release of the connection also makes the operator notice that a specific maximum displacing force has been reached.

In the case of a further variant of the solution according to the invention, the gripping element engages the distal portion of the thread, which in any event must be held by the operator to counter the displacement of the displacing sleeve, and here, too, a release of this connection takes place at the instant at which the maximum displacing force is reached, so that excessive tightening of the loop is avoided; furthermore, here, too, the release of the connection informs the operator that the maximum displacing force has been reached.

In the case of a first preferred embodiment, it may be provided that the connection is formed by a predetermined breaking point that can be destroyed when a specific holding force is exceeded; in another preferred embodiment, however, it is also possible for the connection to be, for example, a flexible latching connection.

It is particularly advantageous if the displacing element is a sleeve closely surrounding the thread, at least at its distal end.

It is also advantageous if the gripping element is a gripping sleeve surrounding the displacing element.

A particularly advantageous configuration is obtained if the gripping sleeve is mounted displaceably in the direction of the thread on a displacing element formed as a sleeve; the two sleeves are then preferably formed concentrically in relation to each other and have a very low space requirement.

In the case of a preferred embodiment, it is provided that the connection of the gripping sleeve and the displacing element is formed by a pair of projections and indentations which are disposed on the inner side of the gripping sleeve and the outer side of the displacing element, engage flexibly in one another, disengage when a specific displacing force is exceeded and permit a relative displacement of the gripping sleeve and the displacing element.

In this case, it is advantageous if the projections and indentations have slide-on surfaces which lie against one another.

It may also be provided that the displacing movement of the gripping element in relation to the displacing element is limited after release of the connection by a stop.

In the case of another embodiment, it is provided that the proximal portion of the thread is disposed in a holding element in such a way that it is secured against displacement in the proximal direction and that the connection that is releasable when a displacing force is exceeded is between the holding element and the gripping element. In the case of this configuration, the operator consequently holds the displacing element on the one hand and the gripping element on the other hand and pulls them apart to tighten the loop, until the displacing force is exceeded; then the gripping element becomes detached from the proximal portion of the thread and in this way prevents excessive tension.

The holding element may be in particular a sleeve surrounding the proximal portion of the thread.

It is also advantageous if the gripping element is a gripping sleeve surrounding the holding element.

An advantageous configuration is obtained if the gripping sleeve is mounted displaceably in the direction of the thread on a holding element formed as a sleeve.

In the case of a particularly preferred embodiment, it is provided that the connection of the gripping sleeve and the holding element is formed by a pair of projections and indentations which are disposed on the inner side of the gripping sleeve and the outer side of the holding element, engage flexibly in one another, disengage when a specific displacing force is exceeded and permit a relative displacement of the gripping sleeve and the holding element.

In particular, the projections and indentations may in this case have slide-on surfaces which lie against one another.

It is also advantageous if the displacing movement of the gripping element in relation to the holding element is limited after release of the connection by a stop.

In the case of a particularly preferred embodiment, it is provided that the loop is led through two implant parts, which can be braced against each other by means of the loop. In this way, a ready-made device is obtained, in which two implant parts to be braced against each other by the loop are already part of the device; this device comprises the thread with the loop, the implant parts held on the latter and the displacing element as well as a gripping element according to the invention with a releasable connection. This entire ready-made unit serves for bringing together and bracing the two implant parts and may be formed as a disposable pack.

In particular, it may be provided that the implant parts have mutually facing plate-shaped butting surfaces, which can be placed from opposite sides against the outer surfaces of two bone parts disposed next to each other; for example, these bone parts may be formed by the cranial bone on the one hand and by a bone plate to be inserted into an opening in the cranial bone on the other hand.

The following description of preferred embodiments of the invention serves for a more detailed explanation in conjunction with the drawing.

BRIEF DESCRIPTION OF THE DRAWINGS

FIG. 1 shows a schematic longitudinal sectional view of a device for pushing together a thread loop with a sleeve-shaped gripping element surrounding a displacing element, in its advanced position;

FIG. 2 shows a view similar to FIG. 1 after release of the connection between the gripping element and the displacing element;

FIG. 3 shows a longitudinal sectional view through a modified exemplary embodiment of a device for pushing together a thread loop with a sleeve-shaped gripping element surrounding a thread holding element, with a connection existing between the gripping element and the holding element, and FIG. 4 shows a view similar to FIG. 3 after release of the connection between the gripping element and the holding element.

DETAILED DESCRIPTION OF THE INVENTION

The device represented in the drawing comprises a thread 1, for example a thin synthetic thread, which is securely connected at one end, the proximal end 2, to a holding element 3 in the form of a ring, while the other, distal end 4 is inserted through openings 5, 6 of two plate-shaped implants 7, 8 in such a way that this distal end 4 is in the first instance led through both implants 7, 8, then returned along the outside of one implant 7—and back through the two implants 7, 8, with the result of forming a loop 9, which is closed by the distal end 4 of the thread 1 being connected to the thread 1 itself by a knot 10. This knot 10 is formed as a displacing knot, for example in the form of a Roeder knot known per se, so that the knot 10 is displaceable in relation to the thread 1 in the direction of the loop 9, the loop 9 being drawn together, while a displacement of the knot 10 in the opposite direction is not possible.

The thread 1 runs between the loop 9 on the one hand and the holding element 3 on the other hand through a displacing element 11 in the form of a sleeve; the sleeve is conically formed at its distal end 12, toward the loop 9, and has a through-opening 13 which widens in the proximal direction, passes through the entire displacing element 11, surrounds the thread 1 in close proximity in the region of the distal end 12 of the displacing element 11 and is freely displaceable along the thread 1.

Mounted displaceably in the direction of the thread 1 on the sleeve-shaped displacing element 11, coaxially in relation to the displacing element 11, is a gripping element 14, which is likewise formed as a sleeve and carries a flange-shaped widened portion 16 at its distal end 15, toward the loop 9.

On its inside wall 17, the sleeve-shaped gripping element 14 has inwardly protruding projections 18, which can snap into complementary depressions 19 in the outside wall 20 of the sleeve-shaped displacing element 11, so that as a result a displacement of the gripping element 14 in relation to the displacing element 11 is opposed by a resistance.

In the region of the depressions 19, the wall of the sleeve-shaped displacing element 11 is perforated in the form of longitudinal slots 21, so that the wall can flexibly bend slightly radially inward. Furthermore, the projections 18 and depressions 19 have lateral, inclined butting surfaces 22 and 23.

In the distal direction, the depressions 19 are followed by axially parallel longitudinal grooves 24, which end at a distance from the depressions 19 in an outwardly projecting step 25.

In the exemplary embodiment represented, the device described, comprising the thread 1, displacing element 11 and gripping element 14 as well as the two plate-shaped implants 7, 8, forms a prefabricated unit which is made available to the operator in this form in a sterile state. Sterilizable synthetic materials are used; the thread 1 and the implants 7 and 8 may consist of absorbable synthetic materials.

This device may be used for example, as shown in the drawing, for fixing two bone plates 26, 27 disposed next to each other, for example for fixing a bone cover in an opening in the cranial bone. For this purpose, the plate-shaped implants 7, 8 are disposed in relation to the two bone plates 26 and 27 in such a way that one implant 7 butts against one side of the two bone plates 26, 27, the other implant 8 against the other side of these bone plates 26 and 27, so that the bone plates 26 and 27 respectively engage between the two plate-shaped implants 7, 8. The loop 9 of the thread 1 runs in the gap 28 between the bone plate 26 and the bone plate 27, the loop 9 preferably extending in the longitudinal direction of this gap 28. In the drawing, this loop has been turned with respect to the longitudinal direction of the gap 28 in order to show the loop better, but this is only possible in the case of a relatively wide gap 28; if the gap is narrower, it is advantageous to turn the loop into the plane of the longitudinal direction of the gap.

The prefabricated device is supplied in such a form that the displacing element 11 and the gripping element 14 are fixed in relation to each other in the axial direction; this is achieved by the projections 18 entering the depressions 19, as represented in FIG. 1.

After placing the implants 7, 8 against the bone plates 26 and 27, the operator displaces the displacing element 11 with the aid of the gripping element 14 in the direction of the loop 9 and at the same time securely holds the proximal end 2 of the thread 1 by means of the holding element 3, in other words the gripping element 14 and the displacing element 11 on the one hand and the holding element 3 on the other hand are pulled apart. As a result, the knot 10 is displaced in the direction of the loop 9 and the loop 9 is tightened. As it does so, it braces the two plate-shaped implants 7, 8 against each other and in this way fixes the bone plates 26 and 27 lying between them in relation to each other.

During the advancement of the knot 10, the force of resistance becomes greater and greater as the tensioning continues, and finally the displacing force which the operator exerts on the displacing element 11 by way of the gripping element 14 becomes so great that a specific maximum value is exceeded. This leads to an elastic deformation in the region of the outside wall 20 of the displacing element 11; this wall region is slightly deformed radially inward. This allows the projections 18 to leave the depressions 19, this exiting action being aided by the inclined butting surfaces 22 and 23. After leaving, the projections 18 enter the longitudinal grooves 24 of the displacing element 11, and this makes it possible for the gripping element 14 to be displaced in relation to the displacing element 11, to be precise until the projections 18 come up against the step 25.

On the one hand, this disengagement of the projections 18 from the depressions 19 interrupts the advancement of the knot 10, and consequently the tensioning of the loop 9; on the other hand, the operator immediately notices from this disengagement that the maximum value of the displacing force has been reached; he can consequently discontinue the process of tensioning the loop 9. The abutment of the implants 7, 8 is completed. Immediately thereafter, the thread 1 can be cut off at the knot 10; the tensioned loop 9 keeps the two plate-shaped implants 7, 8 clamped together in the body and fixes the two bone plates 26 and 27 in relation to each other.

The embodiment of a device for tensioning a thread loop that is represented in FIGS. 3 and 4 is constructed in a way similar to that of FIGS. 1 and 2; parts corresponding to one another therefore bear the same reference numerals.

In the case of this embodiment, the displacing element 11 is of a simpler construction; this is so because it has no gripping element 14 that is displaceable in relation to the displacing element 11, but instead the displacing element 11 is at the same time also the gripping element for advancing the knot 10. This displacing element 11 is merely indicated in the representation of FIGS. 3 and 4 by dash-dotted lines.

The annular holding element 3 in the case of the exemplary embodiment of FIGS. 1 and 2 is replaced in the case 6f the exemplary embodiment of FIGS. 3 and 4 by a sleeve-shaped holding element 31 with a through-opening 33 widening in the proximal direction in the form of steps. The proximal end 2 of the thread 1 is led through the distal part of this through-opening 33; the thread 1 is closely surrounded in this region by the through opening 33 and carries at its end protruding out of this narrow portion of the through-opening 33 a widened stop element 32, which in the exemplary embodiment illustrated is spherical and which prevents the displacement of the thread 1 in the distal direction by the stop element 32 butting against the step of the through-opening 33.

At the proximal end, the outside wall of the holding element 31 is divided by longitudinal incisions 35 into adjacent tongues 36, which at their proximal, free end protrude outward beyond the circumference of the sleeve-shaped holding element and, as a result, respectively form a radially protruding projection 38.

The sleeve-shaped holding element 31 is accommodated in a sleeve-shaped gripping element 34 in such a way that it is displaceable in the longitudinal direction of the latter. The interior space 37 of this sleeve-shaped gripping element 34 widens in the proximal direction at two steps 39 and 40; the diameter of the portion 41 located between the two steps 39 and 40 in this case corresponds to the outside diameter of the sleeve-shaped holding element 31, which is displaceably guided in this middle portion 41.

The tongues 36 thereby lie with their projections 38 in the proximal portion 42 of the interior space of the sleeve-shaped gripping element 34 and engage behind the step 40 between the middle portion 41 and the proximal portion 42, so that as a result the holding element 31 is restrained against being pushed in in the distal direction.

However, the holding element 31 can be displaced further in in the distal direction, into the middle portion 41, when the tongues 36 are flexibly bent radially inward when a specific tensile force exerted by the thread 1 on the holding element 31 is exceeded; this is so because the projections 38 can then slide on the step 40. To facilitate this, the projections 38 and the step 40 are provided with inclined butting surfaces 43, 44.

The depth to which the holding element 31 is displaced into the middle portion 41 of the gripping element 34 is limited by the holding element 31 coming up against the step 39. However, it would also be readily possible to omit the step 39, so that, when the maximum displacing force is exceeded, the gripping element 34 is simply pulled right off the holding element 31.

When the device described is used, a procedure similar to that in the case of the device of FIGS. 1 and 2 is followed. By moving apart the displacing element 11 on the one hand and the gripping element 34 on the other hand, the loop 9 is tensioned until the maximum value of the displacing force is reached. As soon as this is the case, the axial fixing of the holding element 31 in the sleeve-shaped gripping element 34 is overcome and, as the gripping element 34 is moved further away from the displacing element 11, only the holding element 31 is displaced deeper into the gripping element 34, without the proximal end 2 of the thread 1 being tensioned any further, i.e. the tensioning of the loop 9 is ended. At the same time, the operator notices from the sudden displacement of the gripping element 34 and from the projections 38 sliding by on the step 40 that the maximum tensile force has been reached and that the tensioning process has consequently been completed.

While in the case of the exemplary embodiment of FIGS. 1 and 2 a releasable connection is realized in the region between a gripping element and a displacing element, the exemplary embodiment of FIGS. 3 and 4 shows a releasable connection of this type in the region between a gripping element and the holding element for the proximal end of the thread.

The invention claimed is:

1. A surgical device for tightening a slip knot which is formed by a loop at the distal free end of a thread, said loop being displaceable along the thread, comprising:
   a displacing element which can be displaced on the thread toward the loop,
   a gripping element for use in applying tension to said thread,
   a holding element in the form of a flexible latching arrangement for releasably coupling the gripping element to a proximal portion of the thread remote from the loop,
   said gripping element being adapted to decouple from the holding element when a specific displacing force is exceeded,
   wherein each of the displacing, gripping and holding elements are separate elements slidable relative to each other.

2. The device as claimed in claim 1, wherein the displacing element is a sleeve adapted to closely surround the thread, at least at the distal end of the thread.

3. The device as claimed in claim 2, wherein:
the holding element is adapted to secured secure the proximal portion of the thread against displacement with respect to the holding element in the distal direction, and
a connection between the holding element and the gripping element is adapted to be released to decouple the gripping element from said proximal portion of the thread when said specific displacing force is exceeded.

4. The device as claimed in claim 3, wherein the holding element is a sleeve adapted to surround the proximal portion of the thread.

5. The device as claimed in claim 1, wherein:
the proximal portion of the thread is disposed in said holding element in such a way that it is secured against displacement with respect to the holding element in the distal direction, and
a connection between the holding element and the gripping element is released to decouple the gripping element from said proximal portion of the thread when said specific displacing force is exceeded.

6. The device as claimed in claim 5, wherein the holding element is a sleeve surrounding the proximal portion of the thread.

7. The device as claimed in claim 5, wherein the gripping element is a gripping sleeve surrounding the holding element.

8. The device as claimed in claim 7, wherein the gripping sleeve is mounted displaceably in the direction of the thread on the holding element, and the holding element is formed as a sleeve.

9. The device as claimed in claim 5, wherein the displacing movement of the gripping element in relation to the holding element is limited after release of the connection by a stop.

10. The device as claimed in claim 1, wherein:
the gripping element comprises a gripping sleeve surrounding the holding element; and
said flexible latching arrangement couples the gripping element and the holding element and is formed by projections and indentations which are disposed on the inner side of the gripping sleeve and the outer side of the holding element, said projections and indentations adapted to engage flexibly in one another, and to disengage when a specific displacing force is exceeded to permit a relative displacement of the gripping sleeve and the holding element.

11. The device as claimed in claim 10, wherein the projections and indentations have slide-on surfaces which lie against one another.

12. The device as claimed in claim 1, wherein the loop is led through two implant parts, which can be braced against each other by means of the loop.

13. The device as claimed in claim 12, wherein the implant parts have mutually facing plate-shaped butting surfaces, which can be placed from opposite sides against the outer surfaces of two bone parts disposed next to each other.

14. A surgical device for tightening a slip knot which is formed by a loop at the distal end of a thread, said loop being displaceable along the thread, comprising:
a displacing element,
a gripping element for use in moving said displacing element on the thread toward the loop in order to tighten the knot,
said gripping element being coupled to said displacing element via a flexible latching arrangement and adapted to decouple from the displacing element when a specific displacing force is exceeded to stop the displacing element from continuing to move toward the loop, and
a holding element for holding a proximal end of said thread while said displacing element is moved toward the loop at said distal end of the thread,
each of the displacing, gripping and holding elements being separate elements slidable relative to each other.

15. The device as claimed in claim 14, wherein the gripping element is a gripping sleeve surrounding the displacing element.

16. The device as claimed in claim 15, wherein the gripping sleeve is mounted displaceably in the direction of the thread on the displacing element, and the displacing element is formed as a sleeve.

17. The device as claimed in claim 16, wherein the connection of the gripping sleeve and the displacing element is formed by a pair of projections and indentations which are disposed on the inner side of the gripping sleeve and the outer side of the displacing element, engage flexibly in one another, disengage when a specific displacing force is exceeded and permit a relative displacement of the gripping sleeve and the displacing element.

18. The device as claimed in claim 17, wherein the projections and indentations have slide-on surfaces which lie against one another.

19. The device as claimed in claim 15, wherein the displacing movement of the gripping element in relation to the displacing element is limited after release of the connection by a stop.

20. The device as claimed in claim 14, wherein the displacing element is a sleeve adapted to closely surround the thread, at least at the distal end of the thread.

* * * * *

UNITED STATES PATENT AND TRADEMARK OFFICE
CERTIFICATE OF CORRECTION

PATENT NO. : 7,160,310 B2 Page 1 of 1
APPLICATION NO. : 10/862788
DATED : January 9, 2007
INVENTOR(S) : Nesper et al.

It is certified that error appears in the above-identified patent and that said Letters Patent is hereby corrected as shown below:

Column 7, Line 5: Delete the word "secured"

Signed and Sealed this

Twenty-seventh Day of March, 2007

JON W. DUDAS
*Director of the United States Patent and Trademark Office*